United States Patent [19]

Kimura et al.

[11] 4,009,205
[45] Feb. 22, 1977

[54] PROCESS FOR PREPARING 4-AMINO-3-METHYL-N-SUBSTITUTED OR UNSUBSTITUTED ALKYLANILINES

[75] Inventors: Shiro Kimura; Hideo Nagasawa; Yasuo Kato; Yasuyoshi Nakamura; Shoji Miki; Yumiko Ishikawa, all of Tokyo, Japan

[73] Assignee: Sanko Chemical Company Ltd., Tokyo, Japan

[22] Filed: Oct. 10, 1974

[21] Appl. No.: 513,787

[30] Foreign Application Priority Data

Nov. 14, 1973 Japan ............................ 48-127373

[52] U.S. Cl. ............................ 260/556 A; 260/509; 260/510; 260/573; 260/577; 96/22; 96/55; 96/56.6; 96/66 R
[51] Int. Cl.$^2$ .............. C07C 143/75; C07C 143/58; C07C 143/64; G03C 5/30
[58] Field of Search ................ 260/56 A, 577, 580, 260/573, 509, 510

[56] References Cited

UNITED STATES PATENTS

| | | | |
|---|---|---|---|
| 2,193,015 | 3/1940 | Weissberger | 260/556 A X |
| 2,548,574 | 4/1951 | Weissberger et al. | 260/556 A X |
| 2,552,240 | 5/1951 | Weissberger et al. | 260/556 A |
| 2,592,364 | 4/1952 | Weissberger et al. | 260/556 A X |
| 2,794,834 | 6/1957 | Randall et al. | 260/556 A |
| 3,007,914 | 11/1961 | Dittmar et al. | 260/556 A X |
| 3,875,227 | 4/1975 | Kroll et al. | 260/556 A |
| 3,920,739 | 11/1975 | Suda et al. | 260/556 A |

OTHER PUBLICATIONS

*The Chemistry of Amides*, Zabicky (ed.), Interscience, pp. 824–825 (1970).
Bent et al., *J. Am. Chem. Soc.*, 73, pp. 3100–3125 (1951).

Primary Examiner—Daniel E. Wyman
Assistant Examiner—Thomas A. Waltz
Attorney, Agent, or Firm—Sughrue, Rothwell, Mion, Zinn & Macpeak

[57] ABSTRACT

A process for the preparation of 4-amino-3-methyl-N-substituted or unsubstituted alkylanilines comprising acylating and/or sulfonylating 4-amino-3-methyl-nitrobenzene having the formula (I)

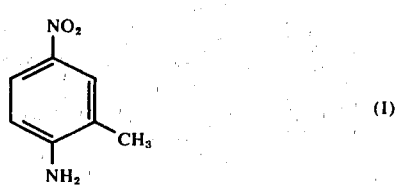

with an acylation or sulfonylation agent to obtain a compound having the general formula (II)

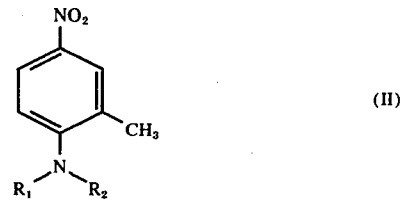

wherein $R_1$ represents a hydrogen atom or an acyl group, $R_2$ represents an acyl group or a sulfonyl group, or $R_1$ and $R_2$ can combine as a difunctional acyl group; reducing the nitro group of the compound having the general formula (II) with hydrogen in the presence of a metal hydrogenation catalyst to obtain a compound having the general formula (III)

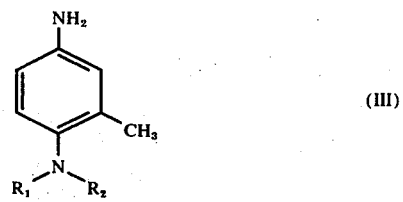

wherein $R_1$ and $R_2$ are as above defined; alkylating the amino group of the compound having the general formula (III) with an alkylation agent selected from the group consisting of an alkyl halide, a substituted alkyl halide and an alkylene oxide to obtain a compound having the general formula (IV)

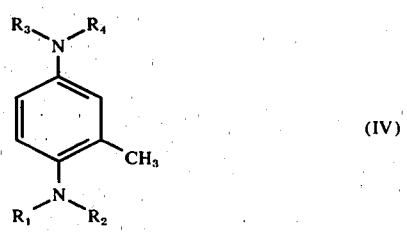

wherein $R_1$ and $R_2$ are as above defined, $R_3$ represents an alkyl group or a substituted alkyl group and $R_4$ represents a hydrogen atom, an alkyl group or a substituted alkyl group; and hydrolyzing the compound having the general formula (IV) to obtain a compound having the general formula (V)

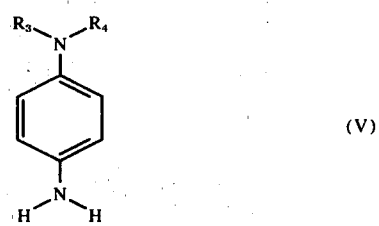

wherein $R_3$ and $R_4$ are as above defined.

11 Claims, No Drawings

PROCESS FOR PREPARING 4-AMINO-3-METHYL-N-SUBSTITUTED OR UNSUBSTITUTED ALKYLANILINES

BACKGROUND OF THE INVENTION

1. Field of the Invention

The present invention relates to a process for preparing 4-amino-3-methyl-N-substituted or unsubstituted alkylanilines, and more particularly, relates to a process for preparing these alkylanilines from 4-amino-3-methyl-nitrobenzene, in which the amino group of the starting 4-amino-3-methyl-nitrobenzene is protected, for example, by tolenesulfonylation, phthalylation or acetylation, the nitro group of the nitrobenzene is hydrogenated and then alkylated, and thereafter the intermediate is hydrolyzed. The products can be converted, if desired, to salts using inorganic or organic acids.

2. Description of the Prior Art

N,N-disubstituted paraphenylene-diamines are important compounds as color developing agents for color photography. In particular, paraphenylene-diamines having a methyl group ortho to the primary amino group are especially important compounds.

Various processes have heretofore been proposed for the production of 4-amino-3-methyl-N-substituted alkylanilines which are commercially available color developing agents for color photography, and of these processes, those disclosed in *Journal of the American Chemical Society*, 73, 3100–3125 (1951) and in Japanese Patent Laid-Open Application Nos. 11534/72 and 11535/72 are particularly popular.

m-Toluidine which is a starting material for the above method is prepared by nitration of toluene and reduction of the m-nitrotoluene produced. In practice, however, m-nitrotoluene corresponds to a mere by-product obtainable in the nitration step of toluene only in an amount of about 3%. Therefore, the yield of m-nitrotoluene is too small and the supply and demand thereof are very often not balanced. Under such circumstances, the above-mentioned process for preparing paraphenylenediamines starting from m-toluidine is not a stable industrial method from the standpoint of cost and the nature of the starting material.

SUMMARY OF THE INVENTION

An object of this invention is to overcome the above-described unstable supply and demand of the starting material in the prior art, and to provide a stable, advantageous and novel process for preparing 4-amino-3-methyl-N-subsituted or unsubstituted alkylanilines.

This invention provides a process for the preparation of 4-amino-3-methyl-N-substituted or unsubstituted alkylanilines comprising acylating and/or sulfonylating 4-amino-3-methyl- nitrobenzene having the formula (I)

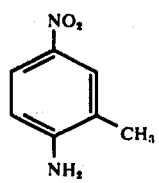

(I)

with an acylation or sulfonylation agent to obtain a compound having the general formula (II)

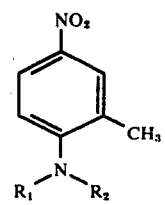

(II)

wherein $R_1$ represents a hydrogen atom or an acyl group, $R_2$ represents an acyl group or a sulfonyl group, or $R_1$ and $R_2$ can combine as a difunctional acyl group; reducing the nitro group of the compound having the general formula (II) with hydrogen in the presence of a metal hydrogenation catalyst to obtain a compound having the general formula (III)

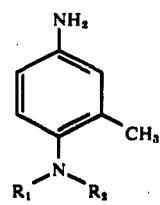

(III)

wherein $R_1$ and $R_2$ are as above defined; alkylating the amino group of the compound having the general formula (III) with an alkylation agent selected from the group consisting of an alkyl halide, a substituted alkyl halide and an alkylene oxide to obtain a compound having the general formula (IV)

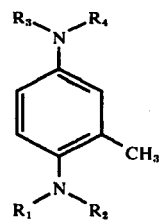

(IV)

wherein $R_1$ and $R_2$ are as above defined, $R_3$ represents an alkyl group or a substituted alkyl group and $R_4$ represents a hydrogen atom, an alkyl group or a substituted alkyl group; hydrolyzing the compound having the general formula (IV) to obtain a compound having the general formula (V)

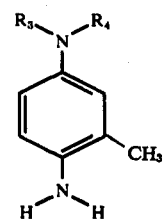

(V)

wherein $R_3$ and $R_4$ are as above defined.

DETAILED DESCRIPTION OF THE INVENTION

As described above, the present invention provides a process for the preparation of 4-amino-3-methyl-N- substituted or unsubstituted alkylanilines starting from 4-amino-3-methyl-nitrobenzene which is industrially and economically available, as shown in the following reaction process schematic:

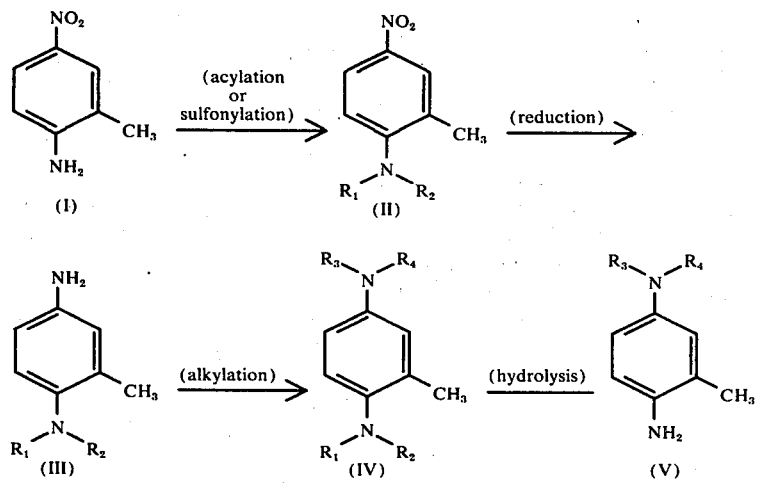

In the above general formulae (I) to (V), $R_1$ represents a hydrogen atom or an acyl group such as a —COCH$_3$ group; $R_2$ represents an acyl group such as a —COCH$_3$ group or a sulfonyl group such as a

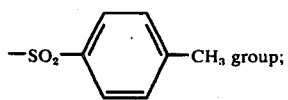

or $R_1$ and $R_2$ can jointly form a diacyl group such as a

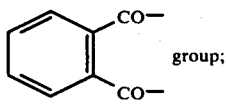

$R_3$ represents an alkyl group such as an unsubstituted lower alkyl group having 1 to 3 carbon atoms such as an ethyl group, or a substituted alkyl group such as a hydroxyalkyl group having 2 to 3 carbon atoms such as a —C$_2$H$_4$OH group or a —C$_3$H$_6$OH group, a —C$_2$H$_4$NHSO$_2$CH$_3$ group or a —C$_2$H$_4$SO$_3$H group; and $R_4$ represents a hydrogen atom, an unsubstituted alkyl group such as a lower alkyl group having 1 to 3 carbon atoms such as a methyl group, an ethyl group or a propyl group, or a substituted alkyl group such as a hydroxyalkyl group having 2 to 3 carbon atoms such as a —C$_2$H$_4$OH group.

For protection of the amino group in the first step, i.e., the acylation or sulfonylation step, acetylation is the most preferred among the above described means, but other protective groups such as a P-toluenesulfonyl group or a phthaloyl group, can optionally be used, if desired.

In the acetylation, the 4-amino-3-methyl-nitrobenzene (I) is dissolved in a suitable solvent such as tetrahydrofuran, acetic acid is added thereto, and acetic anhydride is added dropwise to complete the reaction. The reaction proceeds for about 1 to 6 hours at a temperature of about 60° to 90° C. Other acylations or sulfonylations can be conducted in a similar manner.

The hydrogenation in the second step, i.e., the reduction step, is easily carried out using hydrogen under a pressure of about 15 to 80 Kg/cm$^2$, preferably 50 to 80 Kg/cm$^2$, at a reaction temperature of about 50° to 120° C, preferably 100° to 120° C, for about 1 to 3 hours in the presence of a metal hydrogenation catalyst such as a Raney nickel catalyst, and, if desired, an alkyl aldehyde such as acetaldehyde, etc., which is used in the next step, i.e., the alkylation step, can be incorporated in the reaction system from the beginning.

In the third step, i.e., the alkylation step, an alkyl halide such as ethyl chloride can be used as an alkylating agent, and a substituted alkyl halide such as ethylene chlorohydrin, β-methanesulfonamidoethyl chloride, etc., or an alkylene oxide such as ethylene oxide can be used as a substituted alkylating agent. The alkylation reaction is carried out under normal pressure or increased pressure whereby a 4-alkylamino-3-methyl-N-substituted or unsubstituted alkylaniline is prepared with ease. The reaction conditions greatly vary depending upon the materials used, but can be easily determined by one skilled in the art based on similar alkylations.

In the fourth step, i.e., the hydrolysis step, typical examples of a hydrolyzing agent are hydrochloric acid and sulfuric acid, for example, about 40 to 60% by weight sulfuric acid, preferably 50% by weight sulfuric acid. The hydrolysis reaction is carried out at a temperature of about 80° to 120 ° C for about 3 hours using such a hydrolyzing agent. Further, if desired, an alkali can be used to render the system basic. Alternatively, other inorganic or organic acids such as hydrobromic acid, sulfurous acid, para-toluenesulfonic acid and oxalic acid can optionally be used. As described above, the process of this invention is substantially composed of four reaction steps.

The invention is explained in greater detail in the following Examples which, however, are not intended to be interpreted as limiting the scope of the present invention. Unless otherwise indicated, all parts, percents, ratios and the like are by weight.

EXAMPLE 1

A. Preparation of 4-Acetamino-3-methyl-nitrobenzene 349.6g (2.3 moles) of 4-amino-3-methyl-nitrobenzene were dissolved in 500g of tetrahydrofuran, 500g of acetic acid were added thereto, and 500g (3.5 moles) of acetic anhydride were added dropwise while stirring and heating at 70° to 80° C, and, after the completion of the acetic acid addition, the entire reaction system was reacted for 1 hour under reflux and then was allowed to cool whereby crystals were formed. The crystals were separated, filtered out and then dried.

Yield: 367g; M.P.: 200°–202° C.

B. Preparation of 4-Acetamino-3-methylaniline 19.4g (0.1 mole) of 4-acetamino-3-methyl-nitrobenzene, 30g of dimethylformamide and 1g of fresh-developed Raney nickel were fed in an autoclave, 50kg/cm$^2$ of hydrogen was then fed thereto, and, after the reaction was carried out at 60° to 120° C while stirring, the reaction mixture was removed immediately, the Raney nickel was removed while hot, and thereafter the product was poured into 100ml of methanol to separate the 4-acetamino-3-methylaniline produced.

Yield: 16.0g; M.P.: 140°–140.5° C; Elemental Analysis: Found — C: 65.2%; H: 7.5%; N: 17.1%; Calc'd — C: 65.83%; H: 7.37%; N: 17.06%.

C. Preparation of 4-Acetamino-3-methyl-N-ethylaniline 30g of 4-acetamino-3-methylaniline, 12.1g of 90% acetaldehyde, 2g of sodium acetate, 5g of fresh-developed Raney nickel and 80ml of methanol were fed in an autoclave, and the autoclave was pressurized to 80kg/cm$^2$ with hydrogen and stirred for 2 to 3 hours at room temperature (about 20° to 30° C) whereby absorption of hydrogen ceased and the reaction was completed. The reaction solution was removed, the Raney nickel was removed and then methanol was distilled out to obtain white crystals. The product was recrystallized from ethyl acetate to obtain 30g of white crystals.

M.P.: 102°–103° C; Elemental Analysis: Found — C: 68.1%; H: 8.1%; N: 14.1%; Calc'd — C: 68.72%; H: 8.39%; N: 14.57%.

D. Preparation of 4-Acetamino-3-methyl-N-(β-methanesulfonamidoethyl)-N-ethylaniline A mixture of 57.6g of 4-acetamino-3-methyl-N-ethylaniline, 52g of βmethanesulfonamidoethyl chloride, 27.7g of sodium hydrogen carbonate, 70g of water and 70ml of methanol were refluxed for 5 hours, and thereafter the methanol was distilled out under reduced pressure. Water was added to the reaction system and an oily product separated out. This oily product was poured into ethyl acetate and cooled to obtain white 4-acetamino-3-methyl-N-(β-methanesulfonamidoethyl)-N-ethylaniline.

Yield: 64g; M.P.: 104° –105° C; Elemental Analysis: Found — C: 53.57% H: 7.44%; N: 13.36%; Calc'd — C: 53.65%; H: 7.40%; N: 13.41%.

E. Preparation of 4-Amino-3-methyl-N-(β-methanesulfonamidoethyl)-N-ethylaniline sesquisulfate H$_2$O 60g of 4-acetamino-3-methyl-N-(β-methanesulfonamidoethyl)-ethyl-N-ethylaniline, 47g of sulfuric acid and 36g of water were mixed and stirred and reacted for 3 hours at 100° to 120° C. Thereafter, 65ml of methanol and 140ml of isoproyl alcohol were added thereto and the mixture stirred while cooling whereby 4-amino-3-methyl-N-(β-methanesulfonamidoethyl)-N-ethylaniline·sesquisulfate·H$_2$O separated out. The product was filtered and dried to obtain 73g of white crystals.

M.P.: 128°–130° C.

No melting point depression was observed when this product was mixed with an authentic sample obtained by recrystallization of a commercially available sample of this product from isopropanol, and the melting point determined. The infrared absorption of both products completely corresponded.

Elemental Analysis: Found —C: 32.9%; H: 6.0%; N: 9.7%; Calc'd — C: 33.0%; H: 6.0%; N: 9.6%.

EXAMPLE 2

A. Preparation of 4-(N-p-Toluenesulfonyl)amino-3-methylnitrobenzene 152g (1 mole) of 4-amino-3-methyl-nitrobenzene, 80g of sodium carbonate and 500g of water are mixed, 230g (1.2 moles) of p-toluenesulfonyl chloride were added thereto while stirring, and the reaction was carried out for 3 hours at 70° C to obtain 290g of 4-(N-p-toluenesulfonyl)amino-3-methylnitrobenzene.

M.P.: 173°–174° C

B. Preparation of 4-(N-p-Toluenesulfonyl)amino-3-methylaniline 30.6g (0.6 mole) of 4-(N-p-toluenesulfonyl)amino-3-methyl-nitrobenzene 1g of fresh-developed Raney nickel and 60ml of tetrahydrofuran were charged into an autoclave and the autoclave was pressurized to 60kg/cm$^2$ with hydrogen. The reaction was carried out at 50° to 100° C while stirring. After completion of the reaction, the Raney nickel was removed from the reaction solution and the tetrahydrofuran was distilled out to obtain brown 4-(N-p-toluenesulfonyl)amino-3-methylaniline. The product was recrystallized from ethyl acetate to obtain 24g of yellow-brown crystals.

M.P.: 147°–148° c; Elemental Analysis: Found — C: 60.4%; H: 5.9%; N: 10.5%; Calc'd — C: 60.84%; H: 5.83%; N: 10.13%.

C. Preparation of 4-(N-p-Toluenesulfonyl)amino-3-methyl-N-ethylaniline 23g of 4-(N-p-toluenesulfonyl)amino-3ethylaniline, 6.1g of 90% acetaldehyde, 0.8g of anhydrous sodium acetate were fed into an autoclave and then the autoclave was pressurized to 80 to 90kg/cm$^2$ with hydrogen. The reaction was carried out at 20° to 50° C. After completion of the reaction, the crystals separated were dissolved by adding 100ml of tetrahydrofuran thereto, and, after the Raney nickel was removed, methanol and tetrahydrofuran were distilled out whereby crystals of 4-(N-p-toluenesulfonyl)amino-3-methyl-N-ethylaniline separated out. The product was recrystallized from ethyl acetate to obtain 20g of white crystals.

M.P.: 162°–163° C; Elemental Analysis: Found — C: 62.8%; H: 6.6%; N: 9.3%; Calc'd — C: 63.13% H: 6.62%; N: 9.20%.

D. Preparation of 4-Amino-3-methyl-N-(β-methanesulfonamidoethyl)-N-ethylaniline·sesquisulfate·H$_2$O A mixture of 7g of 4-(N-p-toluenesulfonyl)amino-3-methyl-N-ethylaniline, 4g of β-methanesulfonamidoethyl chloride, 2.1g of sodium hydrogen carbonate, 16g of water and 30ml of methanol were refluxed for 5 hours, and then 16g of sulfuric acid were added thereto and the entire reaction system was again refluxed. Next, the reaction solution was condensed to half the original volume and 300ml of isopropyl alcohol were added thereto to separate crystals. The crystals were filtered out and dried to obtain 1.5g of 4-amino-3-methyl-N-(β-methanesulfonamidoethyl)-N-ethylaniline·sesquisulfate·H$_2$O.

M.P.: 128°–130° C.

In an examination of this product mixed with an authentic sample obtained by recrystallization of the corresponding commercial product from isopropanol, no melting point depression was observed, and the infrared absorption spectrum of both products completely corresponded.

EXAMPLE 3

A. Preparation of 4-Acetamino-3-methyl-N-(β-hydroxyethyl)-N-ethylaniline:

15.2g (0.08 mole) of 4-acetamino-3-methyl-N-ethylaniline obtained in Example 1, Part C, 4.2g (0.09 mole) of ethylene oxide and 50ml of ethanol were fed into an autoclave and reacted for 1 hour at 120° to 130° C in the closed autoclave. Thereafter, ethanol was distilled off to obtain crystals of 4-acetamino-3-methyl-N-(β-hydroxyethyl)-N-ethylaniline. The crystals were recrystallized from ethyl acetate to obtain 18.5g of white crystals.

M.P.: 121°–122° C; Elemental Analysis: Found — C: 66.0%; H: 8.4%; N: 11.5%; Calc'd — C: 66.07%; H: 8.53%; N: 11.86%.

B. Preparation of 4-Amino-3-methyl-N-(β-hydroxyethyl)-N-ethylaniline Sulfate 23.6g (0.1 mole) of 4-acetamino-3-methyl-N-(β-hydroxyethyl)-N-ethylaniline were dissolved in 30g of 50% sulfuric acid. The system was reacted for 5 hours at 80° to 100° C while stirring, and then put into 300 ml of isopropyl alcohol and stirred therein while cooling. Crystals separated out, which were then filtered and dried to obtain 22.2g of 4-amino-3-methyl-N-(β-hydroxyethyl)-N-ethylaniline sulfate.

M.P.: 154°–155° C.

In the examination of this product mixed with an authentic sample obtained by recrystallization of the corresponding commercial product from isopropanol, no melting point depression was observed, and the infrared absorption spectrum of both products completely corrsponded.

EXAMPLE 4

Preparation of 4-Amino-3-methyl-N-(β-hydroxyethyl)-N-ethylaniline Sulfate 30G (0.1 mole) of 4-(N-p-toluenesulfonyl)amino-3-methyl-N-ethylaniline obtained in Example 2, Part C, 50ml of ethanol and 5.3g (0.12 mole) of ethylene oxide were fed into an autoclave and reacted for 2 hours at 120° to 130° C in the closed autoclave while stirring. Then, after the ethanol had been distilled off, 30g of 50% sulfuric acid were added, dissolved and reacted for 5 hours at 80° to 100° C while stirring. The reaction mixture was put into 300ml of isopropyl alcohol and stirred while cooling, whereby crystals separated out. The crystals were then filtered and dried to obtain 19.7g of 4-amino-3-methyl-N-(β-hydroxyethyl)-N-ethylaniline sulfate.

M.P.: 152°–154° C

In the examination of this product mixed with an authentic sample obtained by recrystallization of the corresponding commercial product from isopropanol, no melting point depression was observed, and the infrared absorption spectrum of both products completely corresponded.

EXAMPLE 5

A. Preparation of 4-Acetamino-3-methyl-(N,N-diethyl)aniline 19.1g (0.1 mole) of 4-acetamino-3-methyl-N-ethylaniline obtained in Example 1, Part C, and 100g of water were mixed, and, after 12.5g of diethyl sulfate were added dropwise thereto while stirring, the entire reaction system was stirred overnight at room temperature. Next, the reaction mixture was neutralized with sodium hydroxide and the crystals separated were recrystallized from methanol to obtain 11.5g of white crystals of 4-acetamino-3-methyl-(N,N-diethyl)aniline.

M.P.: 114°–115° C; Elemental Analysis: Found — C: 69.9%; H: 9.1%; N: 13.1%; Calc'd — C: 70.87%; H: 9.15%; N: 12.72%.

B. Preparation of 4-Amino-3-methyl-(N,N-diethyl)aniline Hydrochloride 22g of 4-acetamino-3-methyl-(N,N-diethyl)aniline were dissolved in 30g of 50% sulfuric acid and stirred and reacted for 5 hours at 80° to 100° C. Then, after 50g of water had been added thereto, the reaction mixture was neutralized with 30% sodium hydroxide and extracted with 150ml of benzole. The benzole used was distilled off from the extract to obtain 14.4g of 4-amino-3-methyl-(N,N-diethyl)aniline. The product was distilled for purification under a reduced pressure of 130° C/2mmHg to obtain 13.5g of 4-amino-3-methyl-(N,N-diethyl) aniline. The free amine was dissolved in 100ml of diethyl ether and was converted to the hydrogen chloride salt thereof by introducing dry hydrogen chloride gas into the system. Then, the salt was filtered out and dried to obtain 17.7g of 4-amino-3-metnyl-(N,N-diethyl)aniline hydrochloride.

M.P.: 261° C.

In the examination of this product mixed with an authentic sample obtained by recrystallization of the corresponding commercial product from isopropanol, no melting point depression was observed, and the infrared absorption spectrum of both products completely corresponded.

EXAMPLE 6

A. Preparation of 4-Phthalimino-3-methyl-nitrobenzene 45.6g (0.3 mole) of 4-amino-3-methyl-nitrobenzene were dissolved in 250g of dimethylformamide, 66.6g (0.45 mole) of phthalic anhydride were added thereto, and the entire reaction system was reacted for 6 hours under reflux and then was allowed to cool whereby 4-phthalimino-3-methyl-nitrobenzene was separated out.

Yield: 66g; M.P.: 195°–196° C; Elemental Analysis: Found —C: 63.5%; H: 3.5%; N: 9.9%; Calc'd — C: 63.83%; H: 3.5%; N: 9.93%.

B. Preparation of 4-Phthalimino-3-methylaniline 70.5g (0.25 mole) of 4-phthalimino-3-methyl-nitrobenzene, 500ml of tetrahydrofuran and 3g of fresh-developed Raney nickel were fed into an autoclave, and the autoclave was pressurized to 70kg/cm$^2$ with hydrogen. The system was reacted for 3 hours at 80° to 100° C, and thereafter, the Raney nickel was removed and then tetrahydrofuran was distilled out to obtain yellow crystals.

Yield: 53.5g; M.P.: 182°–182.5° C; Elemental Analysis: Found — C: 71.0%; H: 4.7%; N: 11.8%; Calc'd — C: 71.42%; H: 4.79%; N: 11.11%.

C. Preparation of 4-Amino-3-methyl-(N,N-diethyl)aniline Hydrochloride 25g (0.1 mole) of 4-phthalamino-3-methylaniline, 10g of water, 31g of diethyl sulfate and 27ml of 30% sodium hydroxide were fed into an autoclave and reacted for 2 hours at 120° to 130° C in the closed autoclave. Thereafter, the reaction solution was removed, 25g of concentrated sulfuric acid were added thereto and the mixture was reacted for 5 hours at 80° to 100° C while stirring. The reaction solution was neutralized with a 30% sodium hydroxide aqueous solution after being cooled to room temperature, and afterwards treated using the same procedure as described in Example 5, Part B, to obtain 15.9g of 4-amino-3-methyl-(N,N-diethyl)aniline hydrochloride.

M.P. 260° C.

In the examination of this produced mixed with an authentic sample obtained by recrystallization of the corresponding commercial product from isopropanol, no melting point depression was observed, and the infrared absorption spectrum of both products completely corresponded.

While the invention has been described in detail and with reference to specific embodiments thereof, it will be apparent to one skilled in the art that various changes and modifications can be made therein without departing from the spirit and scope thereof.

What is claimed is:

1. A process for the preparation of 4-amino-3-methyl-N-substituted or unsubstituted alkylanilines comprising acylating or sulfonylating or acylating and difonylating 4-amino-3-methyl-nitrobenzene have the formula (I)

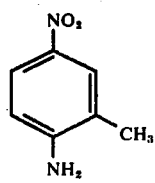

with an acylation or sulfonylation or acylation and sulfonylation agent to obtain a compound having the general formula (II)

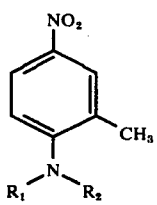

wherein $R_1$ represents a hydrogen atom or an acyl group, $R_2$ represents an acyl group or a sulfonyl group, or $R_1$ and $R_2$ can combine as a difunctional acyl group; reducing the nitro group of the compound having the general formula (II) with hydrogen in the presence of a metal hydrogenation catalyst to obtain a compound having the general formula (III)

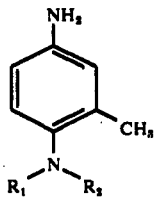

wherein $R_1$ and $R_2$ are as above defined; alkylating the amino group of the compound having the general formula (III) with one or more alkylation steps each using an alkylation agent selected from the group consisting of an alkyl halide, a substituted alkyl halide, an alkyl aldehyde, a dialkyl sulphate and an alkylene oxide to obtain a compound having the general formula (IV)

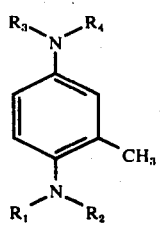

wherein $R_1$ and $R_2$ are as above defined, $R_3$ represents an alkyl group having 1 to 3 carbon atoms or an alkyl group having 2 to 3 carbon atoms and substituted by a hydroxy, a $\beta$-methylsulfonamido as a $SO_3H$ group and $R_4$ represents a hydrogen atom, an alkyl group having 1 to 3 carbon atoms or an alkyl group having 2 to 3 carbon atoms substituted by a hydroxy group; hydrolyzing the compound having the general formula (IV) to obtain a compound having the general formula (V)

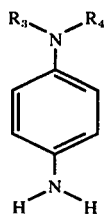

wherein $R_3$ and $R_4$ are as above defined.

2. The process as claimed in claim 1, including converting the compound having the general formula (V) to an inorganic or organic acid salt.

3. The process as claimed in claim 1, wherein $R_1$ represents a hydrogen atom, an acetyl group; $R_2$ represents an acetyl group or a p-toluenesulfonyl group; or $R_1$ and $R_2$ combine to form a phthaloyl group; $R_3$ represents an ethyl group, a hydroxyethyl group, a hydroxypropyl group, a β-methylsulfonamidoethyl group or a $C_2H_4SO_3H$ group; and $R_4$ represents a methyl group, an ethyl group, a propyl group or a hydroxyethyl group.

4. The process as claimed in claim 1, wherein said acylation or sulfonylation or acylation and sulfonylation agent is selected from the group consisting of a p-toluenesulfonylation agent, a phthaloylation agent, or an acetylation agent.

5. The process as claimed in claim 1, wherein said hydrolyzing agent is hydrochloric acid or sulfuric acid.

6. The process as claimed in claim 1, wherein said alkylation agent is an alkyl halide, a substituted alkyl or an alkylene oxide.

7. A process for the preparation of 4-amino-3-methyl-N-substituted or unsubstituted alkylanilines comprising acylating or sulfonylating or acylating and sulfonylating 4-amino-3-methyl-nitrobenzene having the formula (I)

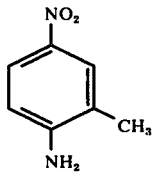

with an acylation or sulfonylation or acylation and sulfonylation agent to obtain a compound having the general formula (II)

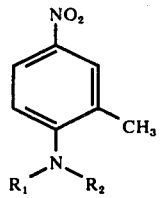

wherein $R_1$ represents a hydrogen atom or an acyl group, $R_2$ represents an acryl group or a sulfonyl group, or $R_1$ and $R_2$ can combine as a difunctional acyl group; reducing the nitro group of the compound having the general formula (II) with hydrogen in the presence of a metal hydrogenation catalyst to obtain a compound having the general formula (III)

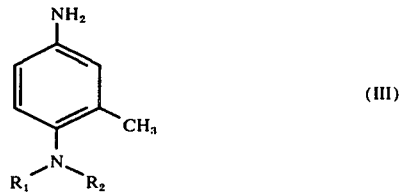

wherein $R_1$ and $R_2$ are as above defined; alkylating the amino group of the compound having the general formula (III) with one or more alkylation steps each using an alkylation agent selected from the group consisting of an alkyl halide, a substituted alkyl halide, an alkyl aldehyde, a dialkyl sulphate and an alkylene oxide to obtain a compound having the general formula (IV)

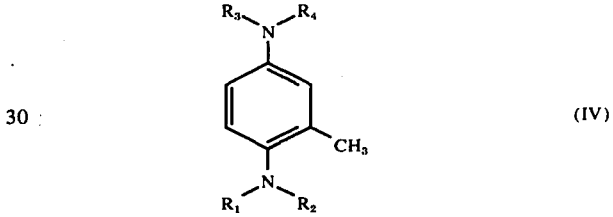

wherein $R_1$ and $R_2$ are as above defined, $R_3$ represents a β-methylsulfonamidoethyl group and $R_4$ represents a hydrogen atom, an alkyl group having 1 to 3 carbon atoms or an alkyl group having 2 to 3 carbon atoms substituted by a hydroxy group; hydrolyzing the compound having the general formula (IV) to obtain a compound having the general formula (V)

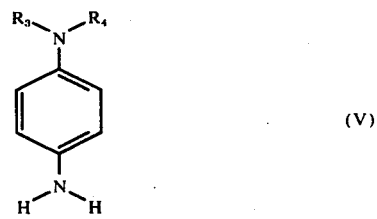

wherein $R_3$ and $R_4$ are as above defined.

8. The process as claimed in claim 1, wherein said alkyl aldehyde is acetaldehyde.

9. The process as claimed in claim 7, wherein said alkyl aldehyde is acetaldehyde.

10. The process as claimed in claim 7, wherein said alkylation agents are acetaldehyde and diethylsulfate.

11. The process as claimed in claim 1, wherein $R_4$ is a hydroxylalkyl group having 2 to 3 carbon atoms.

* * * * *

UNITED STATES PATENT AND TRADEMARK OFFICE
CERTIFICATE OF CORRECTION

PATENT NO. : 4,009,205   Page 1 of 2
DATED : February 22, 1977
INVENTOR(S) : Shiro KIMURA et al It is certified that error appears in the above-identified patent and that said Letters Patent are hereby corrected as shown below:

IN THE HEADING:

Assignee:   "Sanko Chemical Company Ltd.," Should read:

--Sankio Chemical Co., Ltd., Tokyo, Japan --.

IN THE ABSTRACT:

Delete structure (V) and insert therefor

-- 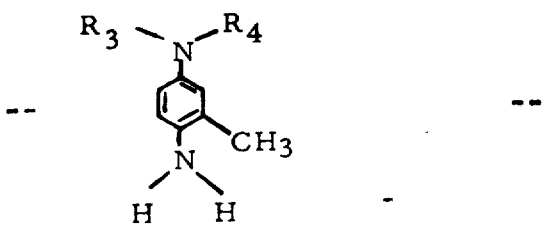 --

Claim 1, next to the last line, delete structure (V) and insert therefor

-- 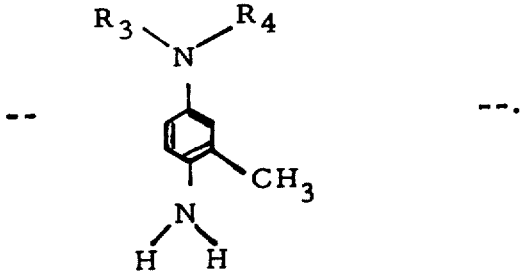 --.

UNITED STATES PATENT AND TRADEMARK OFFICE
CERTIFICATE OF CORRECTION

PATENT NO. : 4,009,205

DATED : February 22, 1977

INVENTOR(S) : Shiro KIMURA et al

It is certified that error appears in the above-identified patent and that said Letters Patent are hereby corrected as shown below:

Claim 7, at the next to the last line thereof, delete structure (V) and insert therefor

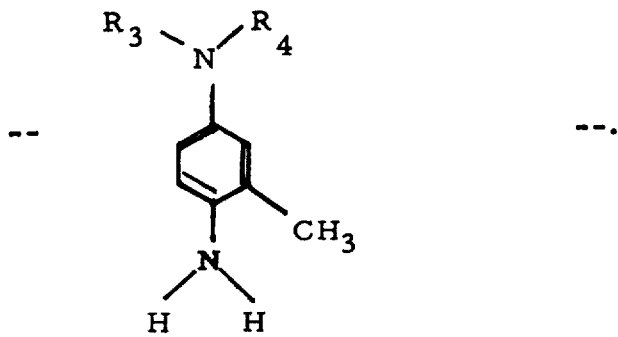

Signed and Sealed this

Twenty-first Day of November 1978

[SEAL]

Attest:

RUTH C. MASON
*Attesting Officer*

DONALD W. BANNER
*Commissioner of Patents and Trademarks*